BLUEGRASS PLANT

Filed Sept. 3 1970 3 Sheets-Sheet 1

INVENTORS
JOSEPHUS J. BARENBRUG
CORNELIS W.H.M. SCHAEPMAN

BY: *Burns, Doane, Swecker & Mathis*
ATTORNEYS

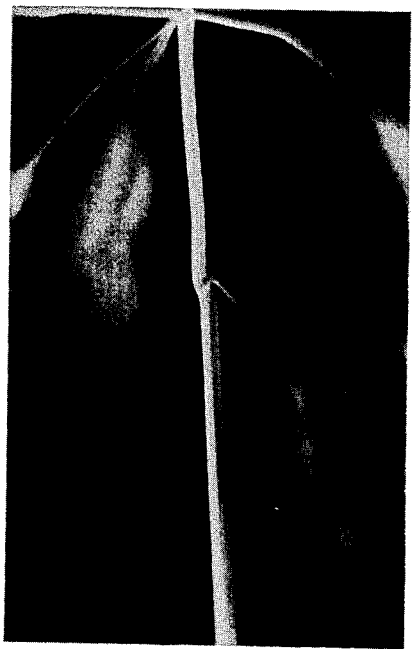
FIG. 3
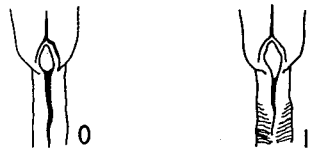
FIG. 4 RED LEAF SHEATH IN YOUTH STAGE
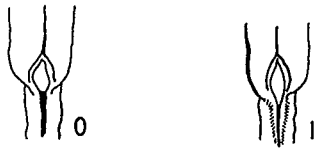
FIG. 5 HAIRS ON MARGIN OF LEAF SHEATH
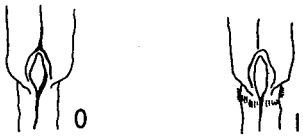
FIG. 6 HAIRTUFT ON THROAT OF SHEATH
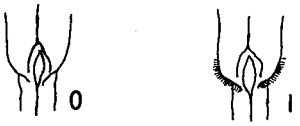
FIG. 9 MARGIN OF LEAF BASE
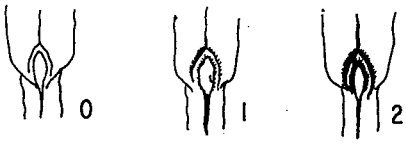
FIG. 7 HAIRS ON LIGULE
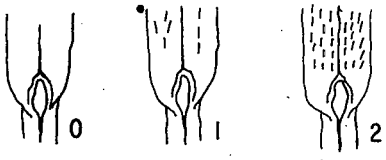
FIG. 10 HAIRS ON UPPER LEAF SURFACE
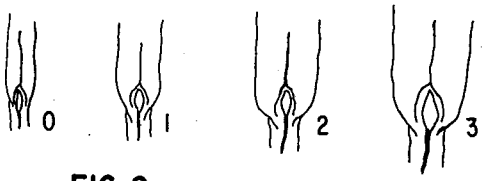
FIG. 8 WIDTH OF LEAF
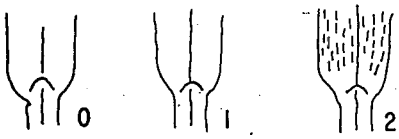
FIG. 11 HAIRS ON LOWER LEAF SURFACE BLUEGRASS PLANT
Filed Sept. 3 1970 3 Sheets-Sheet 3
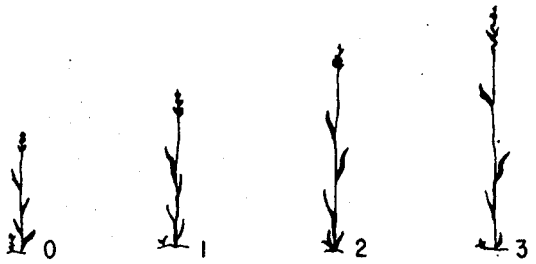
FIG. 12 LENGTH OF CULM OF FULL-GROWN PLANT
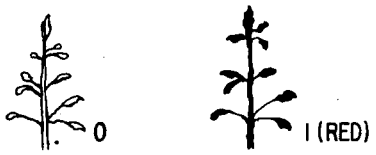
FIG. 13 RED PANICLE
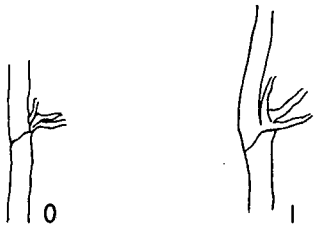
FIG. 14 BEND IN RACHIS OPPOSITE LOWER SIDE BRANCHES
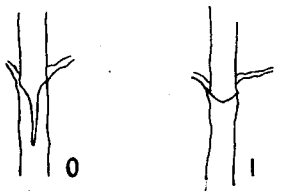
FIG. 15 CLOSED COLLAR OF RACHIS OPPOSITE LOWER SIDE BRANCHES
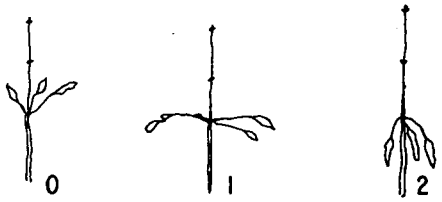
FIG. 16 ANGLE OF LOWER SIDE BRANCHES
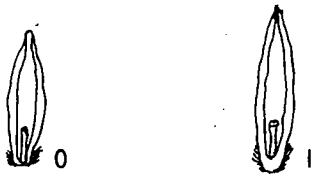
FIG. 17 SIZE OF SEED United States Patent Office Plant Pat. 3,186

Patented May 23, 1972

3,186

BLUEGRASS PLANT

Josephus J. Barenbrug and Cornelis W. H. M. Schaepman, Arnhem, Netherlands, assignors to Barenbrug's Zaadhandel N.V., Arnhem, Netherlands Filed Sept. 3, 1970, Ser. No. 69,507
Int. Cl. A01h 5/00
U.S. Cl. Plt.—88 1 Claim

ABSTRACT OF THE DISCLOSURE

A Kentucky bluegrass plant—Baron—having a unique red panicle and characterized by a broad leaf of dark green color, and being a dwarf variety is highly suitable for establishing sports grounds.

This invention relates to a new and distinct variety of Kentucky bluegrass plant, Baron, which is characterized as being broad leaved, dark green, very slightly susceptible to leafspot, and a hard wearing strain highly suitable for establishing sports grounds.

The instant variety was found when collecting plants on a farm in the eastern part of the Netherlands which had been used for more than eighty years as a calf meadow. The meadow was on sandy soil and situated near a small river, called Vecht, flowing from the German border. The meadow had been permanently grazed.

The collected Kentucky bluegrasses were first tested as single plants, during which time the instant variety attracted attention because of its uniqueness. Plants were cloned and were reproduced asexually. Plants vegetatively produced from parent plants were installed in field plots for both turf evaluation and seed production. New lawns were laid out.

Comparative tests were made with other *Poa pratensis* and the instant variety was found to be superior in many respects. Baron forms a very dense turf which is highly persistent and winter hardy. It has a fine winter color, gets green earlier in the spring than other bluegrass varieties, and is hard wearing. It is a dwarf variety and in certain usages, mowing may be less frequent than with traditional Kentucky bluegrass cultivars. Also, it exhibits a relatively rapid generation response as compared to the usual speed of such bluegrass cultivars. In addition, the instant variety is very slightly susceptible to Helminthosporium leafspot, and will withstand low mowing very well.

After several years of testing the new variety, the Netherlands Board for the Plant Breeder's Right was notified. The new variety Baron was then examined by the I.V.R.O. (Institute for Research on Varieties of Field Crops) at Wageningen, for such properties as distinctiveness, uniformity and stability. The tests were positive, and entry in the Netherlands Register of Varieties followed on Dec. 10, 1969.

A major object of the invention is to provide a new and distinct bluegrass plant having the desirable characteristics referred to above and described in detail below.

Other objects and advantages of the invention will become apparent from the following description when taken in conjunction with the accompanying illustrations in which:

FIG. 3 shows a bend in the rachis which is another unique characteristic of the novel variety of the present invention; and FIGS. 4–17 represent characters used for comparative morphological identification of *Poa pratensis* cultivars.

*Morphological characteristics*

Comparative morphological characteristics of 10 *Poa pratensis* cultivars, including the Baron variety (as provided by I.V.R.O.), are shown in Table I. Reference is made to FIGS. 4–17, where the particular characteristic being compared is schematically shown. The far right-hand column in Table I compares the relative mean dates of ear emergence, in which 0 stands for early, 1 for medium early, 2 for medium late, and 3 for late.

TABLE I

| Shown in Figure | 4 | 5 | 6 | 7 | 8 | 9 | 10 | 11 | 12 | 13 | 14 | 15 | 16 | 17 | |
|---|---|---|---|---|---|---|---|---|---|---|---|---|---|---|---|
| Variety | Red sheath in youth stage | Hairs on sheath margin | Hairtuft on throat of sheath | Hairs on ligule | Width of leaf | Hairs on margin of leaf base | Hairs on upper leaf surface | Hairs on lower leaf surface | Full-grown length of culm | Red panicle | Bend in rachis | Closed collar at rachis | Angle of lower side branches | Size of seed | Date of ear emergence |
| Arista | 1 | 1 | 1 | 2 | 2 | 1 | 0 | 0 | 0 | 0 | 0 | 1 | 1 | 1 | 2 |
| Baron | 0 | 1 | 1 | 1 | 3 | 1 | 0 | 0 | 0 | 1 | 1 | 0 | 1 | 1 | 3 |
| Delft | 1 | 1 | 1 | 0 | 2 | 1 | 0 | 0 | 1 | 0 | 0 | 0 | 1 | 1 | 1 |
| Delta | 1 | 0 | 0 | 0 | 1 | 0 | 1 | 0 | 2 | 0 | 0 | 0 | 1 | 0 | 0 |
| Fylking | 0 | 1 | 1 | 0 | 2 | 1 | 0 | 0 | 1 | 0 | 0 | 0 | 1 | 1 | 1 |
| Merion | 0 | 1 | 0 | 0 | 2 | 1 | 1 | 0 | 1 | 0 | 1 | 1 | 1 | 0 | 3 |
| Newport | 1 | 1 | 0 | 1 | 2 | 1 | 0 | 0 | 2 | 0 | 0 | 0 | 1 | 1 | 2 |
| Park | 1 | 0 | 0 | 0 | 1 | 1 | 2 | 0 | 2 | 0 | 0 | 0 | 1 | 1 | 1 |
| Prato | 0 | 0 | 1 | 0 | 2 | 1 | 0 | 0 | 0 | 0 | 0 | 0 | 2 | 1 | 2 |
| Windsor | 0 | 0 | 1 | 0 | 2 | 1 | 1 | 0 | 2 | 0 | 0 | 0 | 1 | 1 | 1 |

As shown in Table I, Baron deviates from Fylking and Windsor by the following six morphological characteristics:

Hairs on ligule (FIG. 7).—Baron Kentucky bluegrass has hairs on its ligule. Fylking and Windsor do not have.

Width of lead (FIG. 8).—Baron Kentucky blugrass is broad leaved. Fylking and Windsor are less broad leaved.

Length of culm (FIG. 12).—Baron Kentucky bluegrass is a dwarf variety. Fylking and Windsor grow higher.

Panicle (FIG. 13).—Baron Kentucky bluegrass has a deep purplish red panicle, 5RP 3/9 on the Knickerson color fan. Fylking and Windsor have not.

Bend in rachis (FIG. 14).—Baron Kentucky bluegrass shows very clearly a bend in its rachis opposite the lower side branches.

Date of ear emergence.—Baron Kentucky bluegrass has a late date of ear emergence. Fylking and Windsor are medium early.

As is apparent from Table I, Baron deviates in many important respects from other known varieties of Kentucky bluegrass, including the Merion variety.

Figure 2:
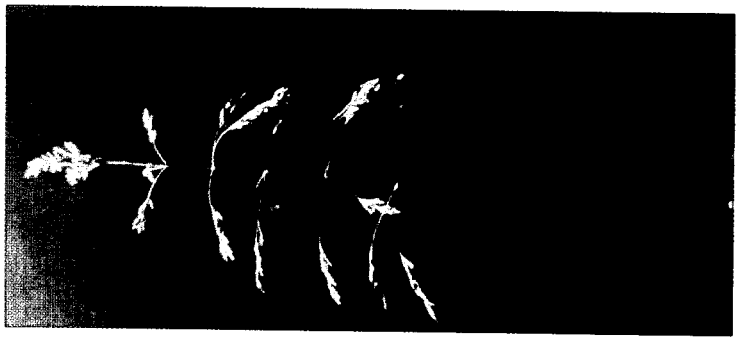
FIG. 2 shows a mature panicle which has a unique red color.

The variety has two very distinctive morphological features. As shown in FIG. 3 of the drawings, it has a bend in its rachis, which is exhibited by only one other variety (Merion). Baron bluegrass also has a panicle of unique purple-red color, as illustrated in FIG. 2, which is exhibited by no other bluegrass species.

The leaves of Baron are 3–6 mm. in width, 5–30 cm. in length. The length of the upper culm leaves is 5–7 cm. The ligule is short and hairy.

Baron bluegrass is small seeded, containing about 1,950,000 seeds per pound (as compared to 2,100,000 for Merion and 1,130,000 for Fylking). The weight of 1,000 corns of Baron is 0.43 g., while that of Merion is 0.20 g.

*Growth behavior*

Baron exhibits a germination emergence and establishment of plants which are somewhat faster than Merion. Since it is known that *Poa pratensis* generally exhibits a show establishment, such a feature offers a large advantage over known varieties in the quick establishment of lawns.

Baron is a dwarf variety which remains shorter and needs less frequent mowing than the known varieties of Kentucky bluegrass, which affords obvious economic advantages. When Baron is mowed, it withstands low mowing very well.

Differences in Kentucky bluegrass varieties in getting green in the spring are of particular interest because spring growth of most varieties of this species occurs late rather than early. Early "getting green" varieties of good quality are significant, since, besides for purely aesthetic reasons, they exhibit quick regeneration of water damaged spots.

The figures in Table II show the results of a "getting green" test made in Western Germany during the spring of 1968, in the month of March.

TABLE II

| Date: | Variety |
|---|---|
| 12 | Baron. |
| 13 | |
| 14 | |
| 15 | |
| 16 | R.v.P. |
| 17 | |
| 18 | Sydsport. |
| 19 | Golf. |
| 20 | Commercial. |
| 21 | |
| 22 | Windsor. |
| 23 | Merion. |
| 24 | Primo. |

As can be seen from Table II, Baron Kentucky bluegrass gets green early in the spring with a distinct advance over the Windsor and Merion varieties.

*Cytological characteristics*

The chromosome number of Baron Kentucky bluegrass ranges between about 68 and 84. However, chromosome numbers of above 100 have been observed in some parts of the plant as well. Variation in chromosome number does not affect the phenotypical characteristics of this highly apomictic plant. The plant is asexually reproduced by rhizomes.

*Turf density*

Baron Kentucky blue grass forms a very dense turf, as may be seen in Table III following, which shows the relative densities of the Kentucky bluegrass varieties through the grass seasons.

TABLE III

| Variety | Spring | Summer | Fall | Average |
|---|---|---|---|---|
| Baron Kentucky bluegrass | 8 | 9 | 10 | 9 |
| Merion bluegrass | 8 | 8 | 9 | 8 |
| Fylking | 8 | 9 | 9 | 9 |
| Windsor | 7 | 7 | 8 | 7 |
| Common | 7 | 6 | 6 | 6 |

(Scale: 10=highest density; 1=lowest density)

*Turf color*

Figure 1:
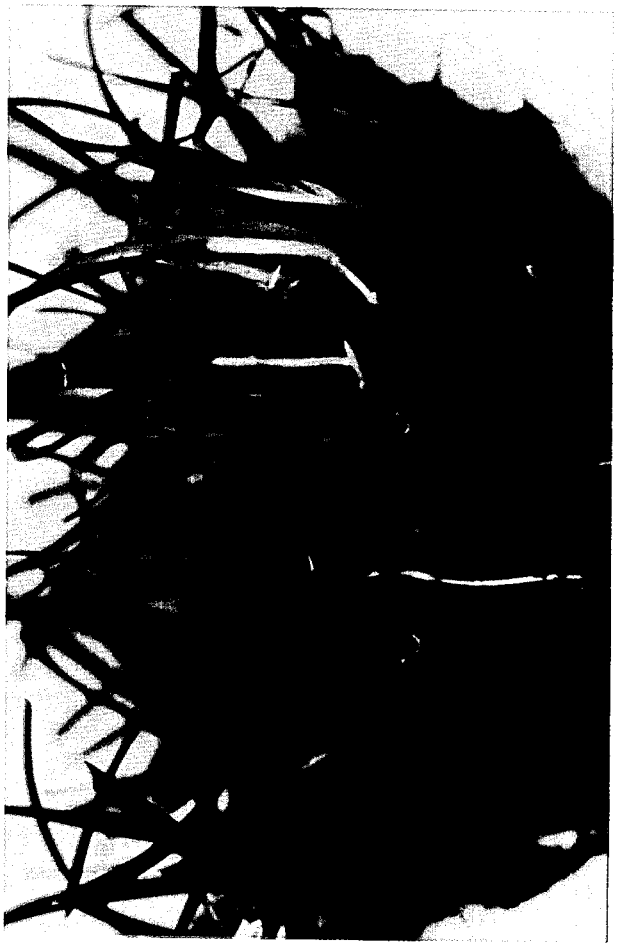
FIG. 1 shows the mature plant with its broad, dark green leaves and rhizomes.

The leaf color of Baron Kentucky bluegrass is very dark blue-green, as seen in FIG. 1. Comparatively speaking, it is darker than any of the known varieties of Kentucky bluegrass, being even darker than the Merion variety.

*Disease resistance*

Baron Kentucky bluegrass is very comparable with Merion bluegrass in its susceptibility to Helminthosporium leafspot. Table IV contains data provided by the German Institut für Grünlandwirtschaft und Futterbau der Justus Liebig Universität Giessen on the susceptibility of Kentucky bluegrass varieties to the fungus Helminthosporium.

| Variety: | Percent tissue destruction |
|---|---|
| Adorno | 40 |
| Arista | 26 |
| Baron | 5 |
| Golf | 37 |
| Merion | 5 |
| Newport | 15 |
| Prato | 34 |
| Primo | 35 |
| R.v.P. | 30 |
| Sydsport | 12 |
| St 1000 | 5 |
| Windsor | 15 |
| Commercial | 70 |

Baron Kentucky bluegrass exhibits a very good resistance to other different diseases, such as *Fusarium roseum*, rust and mildew.

What is claimed is:

1. The variety of bluegrass plant, substantially as shown and described herein, characterized particularly by a red panicle, broad leaves, high resistance to common grass diseases, and early germination and establishment.

No references cited.

ROBERT E. BAGWILL, Primary Examiner